(12) United States Patent
Gaston et al.

(10) Patent No.: US 6,617,355 B1
(45) Date of Patent: Sep. 9, 2003

(54) TREATING ASTHMA BY PREVENTING AND/OR ACCOMODATING S-NITROSOTHIOL BREAKDOWN

(75) Inventors: Benjamin Gaston, Charlottesville, VA (US); Jonathan S. Stamler, Chapel Hill, NC (US); Owen W. Griffith, Milwaukee, WI (US)

(73) Assignees: The University of Virginia Patent Foundation, Charlottesville, VA (US); Duke University, Durham, NC (US); The Medical College of Wisconsin Research Foundation, Inc., Milwaukee, WI (US)

( * ) Notice: Subject to any disclaimer, the term of this patent is extended or adjusted under 35 U.S.C. 154(b) by 0 days.

(21) Appl. No.: 09/403,775

(22) PCT Filed: May 7, 1998

(86) PCT No.: PCT/US98/08978
§ 371 (c)(1),
(2), (4) Date: Nov. 4, 1999

(87) PCT Pub. No.: WO98/52580
PCT Pub. Date: Nov. 26, 1998

Related U.S. Application Data

(60) Provisional application No. 60/081,740, filed on Apr. 15, 1998, and provisional application No. 60/047,336, filed on May 21, 1997.

(51) Int. Cl.[7] ..................... A61K 31/42; A61K 31/197; A61K 31/198
(52) U.S. Cl. ..................... 514/565; 514/378; 514/561; 514/826; 424/660
(58) Field of Search ................... 514/378, 826, 514/561, 565; 424/660

(56) References Cited

U.S. PATENT DOCUMENTS

| 5,380,758 A | 1/1995 | Stamler et al. ............. 514/562 |
| 5,574,068 A | 11/1996 | Stamler et al. ............. 514/562 |

FOREIGN PATENT DOCUMENTS

| CN | 1099997 | * | 3/1995 |
| WO | 92/17445 | * | 10/1992 |

OTHER PUBLICATIONS

Nabe et al., Prostaglandins Leukotrienes and Essential Fatty Acids, 51, 163–171 (1994).*
Minamiyama et al., Am. J. Physiol., 271 (4, Pt. 1), G575–G581, 1996.*
Funayama et al., Am. J. Respir. Cell Mol. Biol., 15(2), 260–267 (1996) (abstract).*
Hogg et al., Biochem. Journal, 323, 477–481 (Apr. 15, 1997).*
American Journal of Respiratory and Critical Care Medicine, Gaston et al., vol. 155, No. 4, p. A945 (4/97).
Gaston, B., et al., The Lancet 351, No. 9112, pp. 1317–1319 (May 2, 1998).

* cited by examiner

*Primary Examiner*—Phyllis G. Spivack

(57) ABSTRACT

Asthma is ameliorated, and mild or moderate asthma is prevented from progressing to more severe asthma by administering agents which prevent and/or accommodate for S-nitrosothiol breakdown.

21 Claims, 2 Drawing Sheets

TREATING ASTHMA BY PREVENTING AND/OR ACCOMODATING S-NITROSOTHIOL BREAKDOWN

This application is a 371 of PCT/US98/08978 filed May 7, 1998 and claims benefit of Prov. No. 60/047,336 filed May 21, 1997 and Ser. No. 60/081,740 filed Apr. 15, 1998.

This invention was made at least in part with Government support under Grants MNCSD S-94-LH-016 and S-93-LH-113 from The Department of the Navy, and under Grants HL02582 and HL52529 from The National Institutes of Health. The United States Government has certain rights in the invention.

TECHNICAL FIELD

This invention is directed to treating a patient with asthma to ameliorate the symptoms thereof, to treating patients with mild or moderate asthma to inhibit progression to more severe asthma, and to reducing corticosteroid requirements in patients with severe asthma.

BACKGROUND OF THE INVENTION

About 10 million asthmatics live in the USA. Asthma sufferers are subject to acute attacks characterized by increased responsiveness of the tracheobronchial tree to various stimuli, which leads to generalized airway constriction manifested by dyspnea, cough and wheezing. Asthma sufferers often experience acute exacerbations of bronchoconstriction, which may be life-threatening. The degrees of severity of an acute asthma attack have been classified as mild, moderate and severe in NIH Publication No. 97-4051 (April 1997) of the National Heart, Lung and Blood Institute of the National Institutes of Health and these classifications are used herein and NIH Publication No. 97-4051 is incorporated herein by reference.

A patient presenting with severe asthma is treated with a series of drugs including inhaled beta$_2$-agonist and anticholinergic and systemic corticosteroid medications, and is given oxygen to achieve O$_2$ saturation $\geq$90%. Any patient with impending or actual respiratory failure is treated with parenteral beta$_2$-agonist, inhaled anticholinergic and parenteral corticosteroid medications, and if no favorable response is shown, by endotracheal intubation and mechanical ventilation and treatment in an intensive care unit. Annually several thousand patients with severe asthma die.

Elder et al. U.S. Pat. No. 5,603,963 states "Recently, gold-based drugs, particularly Auranofin, have also been used to treat asthma . . . ." Auranofin is (1-thio-beta-D-glucopyranose-2,3,4,6-tetraacetato-S) (triethylphosphine) gold. No therapeutic mechanism for this drug is said to have been clearly established.

SUMMARY OF THE INVENTION

It is an object herein to provide novel methods for treating a patient with asthma to ameliorate the symptoms thereof and to treat patients with mild or moderate asthma to inhibit progression to more severe asthma.

It is an object of one embodiment herein to provide a method for treating severe asthma which reduces corticosteroid requirements.

The invention herein is based on the discoveries that severe asthma is associated with a deficiency of endogenous S-nitrosothiols (whereas NO levels are known to be high), that airway tissue contains activities, including enzymatic activities, which break down S-nitrosothiols to NO suggesting that such activities may be elevated in the case of asthma, that activities that break down S-nitrosothiols to NO and other low mass nitrogen oxides attenuate their bronchodilator activity, and that agents which inhibit catalyst for S-nitrosothiol breakdown restore the bronchodilator activity.

In one embodiment, the invention herein is directed to a method for treating a patient with asthma to ameliorate symptoms thereof comprising administering to said patient (a) a therapeutically effective amount of an inhibitor of S-nitrosothiol breakdown except for the gold-containing compounds heretofore used to treat asthma including aurothioglucose, gold sodium thiomalate, and (1-thio-beta-D-glucopyranose-2,3,4,6-tetraacetato-S)(triethylphosphine) gold (Auranofin) or (b) therapeutically effective amounts of an NO donor and of an inhibitor of S-nitrosothiol breakdown, or (c) a therapeutically effective amount of an NO donor which is itself an S-nitrosothiol or which generates on S-nitrosothiol in vivo which is resistant to breakdown by catalysts which cause S-nitrosothiol breakdown.

In another embodiment herein the administrations of (a), (b) or (c) are carried out for the treatment of severe asthma in combination with systemic administration of a therapeutically effective amount of corticosteroid which is 10–80% of the dose of systemic corticosteroid utilized for the treatment of severe asthma if administrations of (a) or (b) or (c) are not utilized.

In still another embodiment, the invention herein is directed to a method for treating patients with mild or moderate asthma to inhibit progression to more severe asthma comprising administering to said patient (a) a therapeutically effective amount of an inhibitor of S-nitrosothiol breakdown except for gold containing compounds heretofore used to treat asthma including aurothioglucose, gold sodium thiomalate and (1-thio-beta-D-glucopyranose-2,3,4,5-tetraacetato-S)(triethylphosphine)gold (Auranofin) or (b) therapeutically effective amounts of an NO donor and of an inhibitor of S-nitrosothiol breakdown or (c) a therapeutically effective amount of an No donor which is itself an S-nitrosothiol or which generates an S-nitrosothiol in vivo which is resistant to breakdown by catalysts which cause S-nitrosothiol breakdown.

Gold-containing compounds which have heretofore been used to treat asthma are excluded in (a), above, to provide novelty. Administration of inhibitors of S-nitrosothiol breakdown different from these gold-containing compounds is not obvious from prior art administration of gold-containing compounds to treat asthma because the therapeutic mechanism of action of said gold-containing compounds in treating asthma has not heretofore been known. Gold-containing compounds are not excluded from inhibitors of nitrosothiol breakdown in (b), above, for the broad invention because gold-containing compounds have not heretofore been administered in combination with NO donors to treat asthma. While S-nitrosothiols have been administered previously to those with asthma to relax non-vascular smooth muscle including airway smooth muscle (see Stamler et al. U.S. Pat. Nos. 5,380,758; 5,574,068; 5,593,876 and 5,612,314), they have not been administered in combination with agents that prevent S-nitrosothiol breakdown to replace or add to the function of endogenous S-nitrosothiols. The combination is not obvious because it was not heretofore appreciated that S-nitrosothiols are subject to accelerated breakdown in asthma and that the combining of S-nitrosothiols with breakdown inhibitors makes more S-nitrosothiol available and provides synergistic result.

The term "S-nitrosothiol" is used herein to mean organic compound with NO group bonded to S.

The term "S-nitrosothiol breakdown" is used herein to mean a biologic process that causes decomposition of S-nitrosothiols such that they have less or no non-vascular smooth muscle relaxing effect. Both enzymatic and non-enzymatic processes are embraced. In one embodiment herein, non-enzymatic breakdown by superoxide is excluded.

The term "inhibitor of S-nitrosothiol breakdown" is used herein to mean a treating agent which inhibits decomposition of S-nitrosothiol breakdown so that the smooth muscle relaxing effect of the S-nitrosothiol persists longer.

The term "therapeutically effective amount" is used herein to mean an asthma symptom ameliorating effective amount and, in-the case of patients with mild or moderate asthma, an amount effective to inhibit progression to more severe asthma. In all cases, a therapeutically effective amount is also an amount that effects an increase in S-nitrosothiol concentration or efficacy in airway tissue.

DETAILED DESCRIPTION

Figure 1:
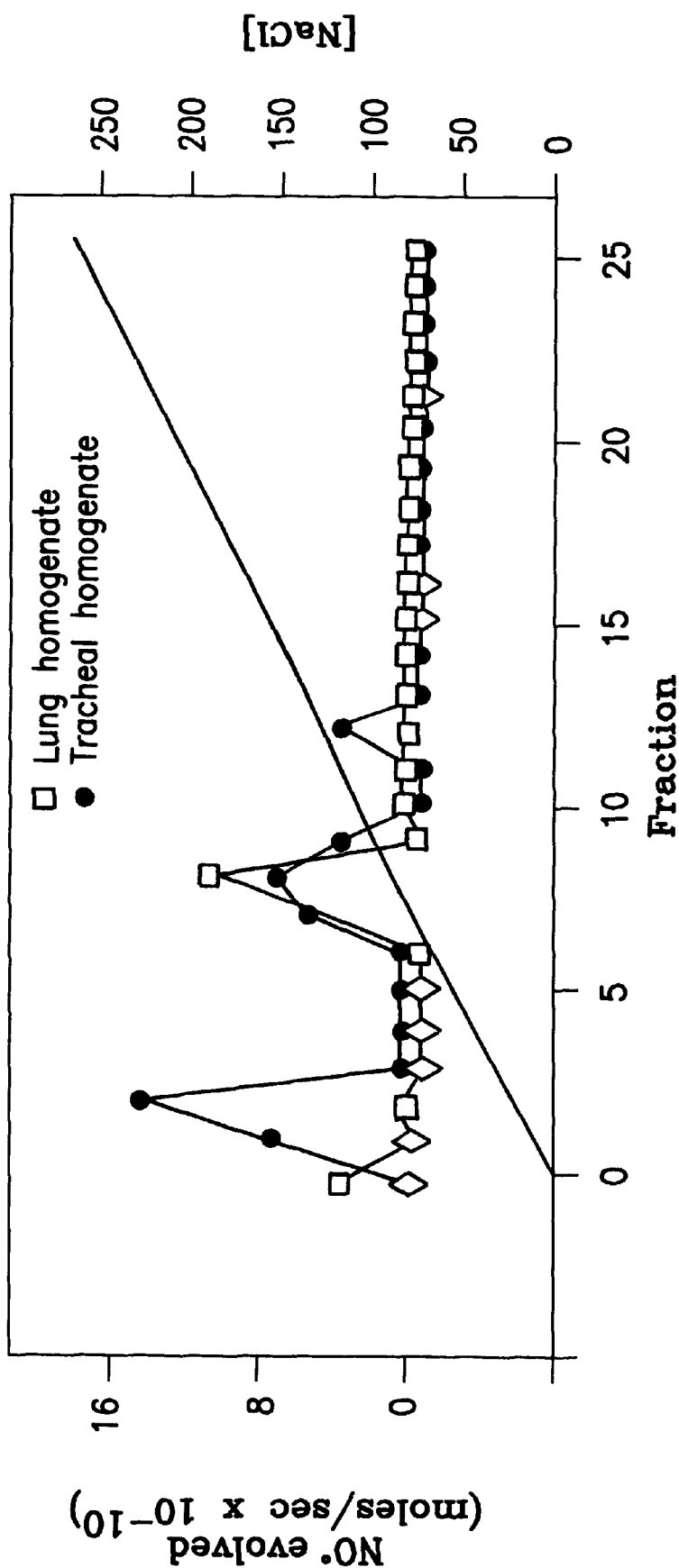
FIG. 1 shows that guinea big trachea and lung parenchyma contain activities that break down S-nitrosothiols to NO and depicts results of Background Example 2.

Inhibitors of S-nitrosothiol breakdown for (a) and (b), above, include inhibitors of gamma-glutamyltranspeptidase. The enzyme gamma-glutamyltranspeptidase removes the glutamyl residue from S-nitrosoglutathione forming S-nitrosocysteinylglycine, a compound prone to release NO quickly. Low mass (<10 kD) S-nitrosothiols have been found to constitute greater than 90% of the S-nitrosothiols in severely asthmatic subjects consistent with previous observations in normal subjects, so inhibiting gamma-glutamyltranspeptidase has a significant effect on inhibiting S-nitrosothiol breakdown. Inhibitors of gamma-glutamyltranspeptidase include, for example, L-gamma-glutamyl-(o-carboxy)phenylhydrazide, D-gamma-glutamyl-(o-carboxy)phenylhydrazide, acivicin and the combination of L-serine and borate. The dosage for inhibitors of gamma-glutamyl transpeptidase is a therapeutically effective amount and generally ranges from 0.01 to 10 mmol/kg body weight when given systemically or 0.01 to 100 µmol/kg body weight when given via inhalation. The route of administration is preferably via inhalation in the form of an aerosol.

Inhibitors of S-nitrosothiol breakdown for (a) and (b), above, include inhibitors of xanthine oxidase. The enzyme xanthine oxidase directly catalyzes the breakdown of S-nitrosocysteine. Inhibitors of xanthine oxidase include allopurinol. Dosage for allopurinol is 100 to 800 mg per day when given orally and 0.01 to 10 mg when given by inhalation.

Inhibitors of S-nitrosothiol breakdown for (a) and (b), above, also include chelators of copper and/or heme or non-heme iron. These include, for example, bathocuproine disulfonate, diethylenetriaminepentaacetic acid, deferoxamine, diethylcarbamodithioic acid sodium salt, edentate calcium disodium, penicillamine, pentetic acid, succimer and trientine. The dosage for chelators of copper and/or heme iron is a therapeutically effective amount and generally ranges from 0.01 µmol/kg to 1 mmol/kg body weight. The route of administration is preferably via inhalation in the form of an aerosol.

Inhibitors of S-nitrosothiol breakdown for (a) and (b), above, also include inhibitors of enzymes and non-enzymatic proteins containing thiol groups and/or selenothiol groups including inhibitors of glutathione peroxidase and thioredoxin reductase which are not gold containing compounds which have previously been used to treat asthma. These include, for example, ethacrynic acid (10 to 200 mg/day dosage for systemic administration and 0.001 to 10 mg via inhalation as an aerosol), melarsoprol (0.01 to 20 mg/kg dosage for systemic administration and 0.0001 to 50 mg via inhalation as an aerosol), sodium stibogluconate (0.01 to 50 mg/kg dosage for systemic administration and 0.0001–50 mg via inhalation as an aerosol), N-ethylmaleimide (0.001–10 mg via inhalation as an aerosol), and iodoacetic acid (0.001–10 mg via inhalation as an aerosol). In one alternative, all gold-based drugs are excluded for (a), above. In another alternative, all gold-based drugs are excluded for (b), above.

Inhibitors of S-nitrosothiol breakdown for (b), above, in one alternative, also include inhibitors of enzymes and non-enzymatic proteins containing thiol groups and/or selenothiol groups including inhibitors of glutathione peroxidase and inhibitors of thioredoxin reductase, which are gold containing compounds which have previously been used to treat asthma including aurothioglucose (Solganal), gold sodium thiomalate (Myochrisine) and (1-thio-beta-D-glucopyranose-2,3,4,6-tetraacetato-S) (triethylphosphine) gold (Auranofin). The dosage for these gold-based drugs is a therapeutically effective amount and normally ranges from 0.001 to 50 mg for Solganal and Myochrisine and from 0.001 to 6 mg for Auranofin. The route of administration is preferably via inhalation in the form of an aerosol. Oral and parenteral routes of administration of said gold-containing compounds are conventional in the case of treating asthma and are also appropriate here.

We turn now to the NO donors for (b), above. These are S-nitrosothiols which are subject to breakdown by catalysts which cause S-nitrosothiol breakdown in asthma when inhibitors of breakdown are not concurrently administered or which form S-nitrosothiols in vivo which have this characteristic. These are preferably S-nitrosothiols. These include, for example, S-nitrosoglutathione, S-nitroso-N-acetylcysteine, S-nitrosohomocysteine, S-nitrosothiomaleate, S-nitrosomethylmercaptan, S-nitrosotrifluoromethylmercaptan, S-nitrosothioglucose, and S-nitroso-derivatives of cysteine containing peptides of 2 to 20 amino acids. The S-nitrosothiols having a molecular weight less than 150 (e.g., S-nitrosomethylmercaptan and S-nitrosothrifluoromethylmercaptan) may be preferred as these are volatile at body temperature and are therefore more readily utilized on inhalation. Where optical isomers exist, the L-isomers constitute the NO donors of (b) and D-isomers constitute the NO donors of (c) which are discussed hereinafter. The NO donors which can form S-nitrosothiols in vivo include, for example, nitroglycerin, amylnitrite, NON-Oates and N-nitroso hexosamines and disaccharide derivatives thereof. The dosage is a therapeutically effective amount. The preferred dosage ranges from 0.001 to 100 mg. The route of administration is preferably via inhalation in the form of an aerosol.

We turn now to the NO donors of (c), i.e., the NO donors which are themselves S-nitrosothiols or which generate S-nitrosothiols in vivo which are resistant to breakdown by catalysts which cause S-nitrosothiol breakdown. These are compounds which are "sterically hindered" so as not to be subject to enzymatic or non-enzymatic breakdown. The NO donors include, for example, $NO_x$ derivatives of asthma drugs selected from the group consisting of $\beta_2$-adrenergic agonists (e.g., metaproterinol, terbutaline, and albuterol), cromolyn, theophylline, atrovent and cysteinyl leukotriene receptor antagonists, where x ranges from 1 to 2, and preferably are S-nitrosothiol derivatives of asthma drugs selected from the group consisting of $\beta_2$-adrenergic agonists, cromolyn, theophylline, atrovent and cysteinyl leukotriene receptor antagonists. The S-nitrosothiol derivatives of asthma drugs are prepared, for example, by substitution of primary or secondary amino groups or hydroxyl groups with a thiol acid (e.g., thiolacetic acid) to give the corresponding amide or ester and provide a thiol group which is converted to S-nitrosothiol by treatment with acidified sodium nitrite. Alternatively hydroxyl groups in the drugs are replaced by SH which is converted to S-nitrosothiol. NO donors which are $NO_x$ derivatives of asthma drugs which are not S-nitrosothiol derivatives of asthma drugs, are prepared, for example, by substitution of hydroxy groups with NO to form nitrite esters or with $NO_2$ to form nitrate esters and by substitution of a primary or secondary amino group with a hydroxy acid (e.g., glycolic acid) followed by conversion of the hydroxy groups to nitrite esters and nitrate esters. The derivatives of asthma drugs can be administered in dosages which are equimolar to the dosages of the asthma drugs from which they are derived and are administered by the same routes of administration as the asthma drugs from which they are derived. Other "sterically hindered" S-nitrosothiols include, for example, compounds in which the thiol is on a tertiary carbon (e.g., S-nitroso-tert-butylmercaptan and S-nitroso-N-acetylpenicillamine), and D-isomers of S-nitroso-compounds mentioned for (b), above; the dosage is a therapeutically effective amount with the preferred dosage ranging from 0.001 to 100 mg, and the route of administration is preferably via inhalation in the form of an aerosol The NO donors (c) may be administered in combination with the NO donors of (b) and/or in combination with the inhibitors of S-nitrosothiol breakdown as set forth for (b), above, in the dosages and with the routes of administration set forth for said inhibitors for (b).

We turn now to the embodiment herein where the administrations of (a), (b) or (c) are carried out for the treatment of severe asthma in combination with systemic administration of a therapeutically effective amount of systemic corticosteroid which is 10–80% of the dose utilized for the treatment of severe asthma where the administration of (a), (b) or (c) are not utilized. Preferably the dosage of corticosteroid is reduced more than one-third compared to where systemic corticosteroid is utilized and the administration of (a), (b) or (c) are not employed. The systemically administered corticosteroids include, for example, prednisone and prednisolone. Initial dosages for prednisone and prednisolone for conventional treatment of severe asthma are listed in Table 28-3 of "Goodman & Gilman's The Pharmacological Basis of Therapeutic" Ninth Edition, which is incorporated herein by reference.

Agents given herein by inhalation may also be given intranasally.

The inventions herein should be considered in light of the following Background Examples and are illustrated, but not limited, by the following Examples.

BACKGROUND EXAMPLE 1

Asthmatic children in respiratory failure were studied within 24 hours of endotracheal intubation. Asthma was defined as (1) a history of three or more albuterol responsive episodes of expiratory flow limitation; (2) an inspiratory- to expiratory-time ratio of less than 0.33; and (3) no evidence of pneumonia. Control subjects had no history of respiratory disease and were undergoing elective, non-thoracic surgery. Three additional subjects who were endotracheally intubated for pneumonia (6.4+/-5.5 years old; pathogens: *Pneumocytis carinii, Pseudomonas aeruginosa*, and aerobic flora) were also evaluated.

Specimens (one from each subject and control) were obtained with routine tracheal suctioning. In most cases, the sample was obtained without airway irrigation.

When irrigation was required (three asthmatic and no control or pneumonia subjects), Methylene Blue (10 $\mu$M)-containing saline was used to determine the degree of dilution ($E_{664}$=41, 700 $M^{-1}$ $cm^{-1}$). Each specimen underwent centrifugation and was frozen (−80° C.) within 15 minutes of sampling to prevent S-nitrosothiol decomposition. Total S-nitrosothiol concentration was measured on all samples.

Amounts of S-nitrosothiols were determined by two separate methods. The first involved photolytic cleavage of the S-nitrosothiol bond followed by measurement of evolved NO by chemiluminescence (Nitrolyte, Thermedix, Woburn, Mass. and a homemade unit). Parallel samples were treated with mercuric dichloride which selectively destroys the S-nitrosothiol bond, extinguishing the NO signal elicited by photolysis. Here, S-nitrosothiols are defined by NO signals that are generated by photolysis and eliminated by mercuric dichloride. This assay is linear over the concentration range 5 nM to 100 $\mu$M ($r^2$=0.99), and does not detect nitrite ($NO_2^-$), nitrate ($NO_3^-$) or 3-nitrotyrosine (3NT). Additionally, some samples were assayed using a cysteine-cuprous chloride (CuCl) technique involving treatment of samples with 1 mmol/liter cysteine and 100 $\mu$mol/liter CuCl (50° C.) which reductively catalyzes release of NO from S-nitrosothiols. The NO measurement is once again made by chemiluminescence. This latter assay was nearly as sensitive ($r^2$=0.99; 10 nM–1 $\mu$M) and as specific (lower limit of $NO_2^-$ detection: 10 $\mu$M) as the photolysis method, failing to detect 100 $\mu$M 3NT or $NO_3^-$.

Asthmatic subjects were found to have airway S-nitrosothiol concentrations (65+/-45 nM; n=8) substantially lower than in control children undergoing elective surgery representing normal non-asthmatic subjects (502+/-429 nM; n=21) as measured by photolysis signal and verified using the CuCl method in three subjects. High S-nitrosothiol concentrations (2486+/-1270 nM) were observed in children with pneumonia.

The experiment shows that asthma is associated with a previously unrecognized deficiency of S-nitrosothiols, endogenous bronchodilators which are over 100-fold more potent than theophylline. This observation indicates that depletion of bronchodilator S-nitrosothiols contributes to the pathophysiology of airflow obstruction. This is a novel finding because asthma is classically characterized by an excess of bronchoconstricting and inflammatory mediators, not by a bronchodilator deficiency.

The above suggested to us that reversal of the defect, i.e., low airway S-nitrosothiols in asthmatics, may be therapeutic.

The subject matter of this Background Example is from a manuscript titled "Bronchodilator S-Nitrosothiol Deficiency in Asthmatic Respiratory Failure," which published in The Lancet on May 2, 1998 by authors Gaston, B., et al.

BACKGROUND EXAMPLE 2

Guinea-pig tracheal and lung parenchymal tissue were separately homogenized in 1 mM ethylenediaminetetraacetic acid, 50 mM TRIS HCl buffer, pH 7.4, 10 mg/liter soybean trypsin inhibitor, 10 mg/liter pepstatin, 10 mg/liter chymostatin and 100 mg/liter phenylmethylsulfonyl fluoride at 4° C. and underwent centrifugation (5,000 g; 5 min) and filtration. The supernatant was loaded onto a DEAE cellulose column and eluted with a linear gradient of 0–250 mM NaCl. The S-nitrosoglutathione degrading activity was assayed as NO evolution. The results are depicted in FIG. 1 (fractions causing a net loss of NO are represented by diamonds). The results show that guinea-pig trachea and lung parenchyma contain activities which break down nitrosothiol to NO, suggesting that such activity may be elevated in asthma.

BACKGROUND EXAMPLE 3

Figure 2:
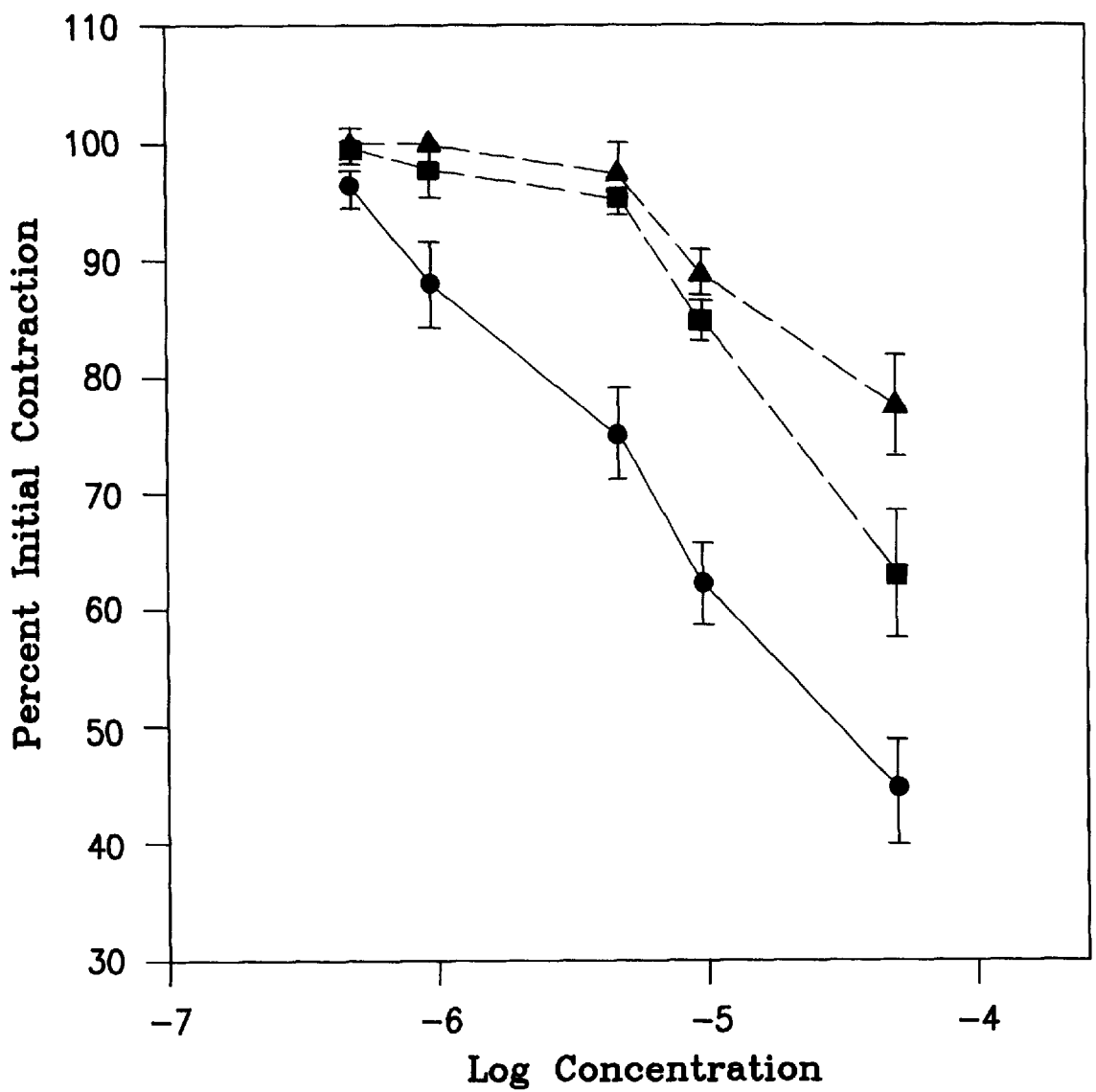
FIG. 2 shows that incubation of S-nitrosoglutathione with fractions that break down S-nitrosothiol to NO attenuate their bronchodilator activity and that inhibition of these activities with aurothioglucose partly reverses the breakdown, and depicts results of Background Example 3.

Guinea-pig tracheal rings were suspended in Krebs-Henseleit buffer (pH 7.4, 37 degrees C., equilibrated with 95% oxygen/5% carbon dioxide) and equilibrated under one gram tension. Smooth muscle contraction was monitored using a force transducer. After contraction with 5 $\mu$M methacholine, rings were exposed to S-nitrosoglutathione which had been incubated (30 minutes, pH 7.4, 25 degrees C.) (a) in phosphate buffered saline alone, (b) with guinea-pig lung protein fractions having S-nitroglutathione breakdown activity isolated as described in Background Example 2, and (c) with active lung fractions and 100 $\mu$M aurothioglucose. The results are shown in FIG. 2, wherein the results of (a) are depicted as circles, the results of (b) are depicted as triangles, and the results of (c) are depicted as squares, (n=7) in each experiment. Data in FIG. 2 are presented as mean, +/– S.E. The data show that relaxation was nearly completely inhibited by incubation with active fractions ($p<0.005$ for all concentrations >500 nM) and was partially restored by aurothioglucose ($p<0.001$ at 50 $\mu$M). The data show that incubation of S-nitrosothiol with fractions that break down S-nitrosothiol to NO attenuate their bronchodilator activity and that inhibition of these activities with aurothioglucose partly reverses the attenuation.

EXAMPLE I

A 13 year old boy with severe asthma developing symptoms of dyspnea, tachypnea, wheezing and cough is administered a 50 mM solution of L-gamma-glutamyl-(o-carboxy) phenylhydrazide as an aerosol via inhalation at a dosage of 0.01 ml/kg. His symptoms improve.

EXAMPLE II

A 24 year old woman with severe asthma with symptoms of dyspnea on exertion, cough and prolonged expiration is administered a 10 mM solution of bathocuproine disulfonate via inhalation as an aerosol at a dose of 0.01 ml/kg. Her symptoms improve.

EXAMPLE III

A 60 year old woman with severe asthma with chronic symptoms of night-time cough, dyspnea and wheezing is maintained on inhalations of an aerosol of a 10 mM solution of each of S-nitrosoglutathione and aurothioglucose, at a dosage of 0.01 ml/kg. Her symptoms improve.

EXAMPLE IV

A 6 year old girl with severe asthma and impending respiratory failure with symptoms of wheezing, cough and cyanosis is given terbutaline (5 $\mu$g/kg/min) by continuous IV-infusion. No improvement occurs. The terbutaline is replaced with an equimolar amount of terbutaline substituted with S-nitrosothiol group. Amelioration of her symptoms is obtained.

EXAMPLE V

A 30 year old man has respiratory failure with symptoms of wheezing, cough and cyanosis. No improvement occurs with parenteral methylprednisone (4 mg/kg) and terbutaline (5 $\mu$g/kg/min). The patient is treated with nebulized acivicin (0.01 mmol/kg) and his symptoms improve.

EXAMPLE VI

A 35 year old man with respiratory failure with symptoms as described in Example V is given inhalation of a 10 mmol solution of S-nitroso-D-cysteine, 0.01 ml/kg. Improvement occurs.

EXAMPLE VII

A 20 year old severe asthmatic with chronic dyspnea is given 30 mg daily prednisone. The dosage is able to be decreased to 30 mg every other day when the patient is treated with inhalation of an aerosol of a 10 mM solution of each of S-nitrosoglutathione and aurothioglucose, at a dosage of 0.01 ml/kg.

EXAMPLE VIII

A severe asthmatic is treated with inhalation of 1 mg allopurinol. Symptoms improve.

EXAMPLE IX

A severe asthmatic is treated with inhalation of a 10 mM solution of each of S-nitrosomethylmercaptan and ethacrynic acid, at a dosage of 0.01 ml/kg. Symptoms improve.

EXAMPLE X

A 10 year old boy wakes up every night coughing and coughs on exertion. The patient is given inhalations of 0.01 ml/kg of a 10 mM solution of S-nitroso-D-cysteine. The patient sleeps through the night and is able to participate in sports without shortness of breath.

EXAMPLE XI

A 40 year old man has wheezing and coughing, which does not limit his activity, three times a year following a respiratory infection. The patient takes nebulized acivicin (0.01 mmol/kg) and becomes asymptomatic.

Variations in the treatment methods will be evident to those skilled in the art. Therefore, the scope of the invention is to be determined by the scope of the claims.

What is claimed is:

1. A method for treating a patient with asthma to ameliorate symptoms thereof comprising administering to said patient a therapeutically effective amount of an inhibitor of S-nitrosothiol breakdown except for aurothioglucose, gold sodium thiomalate and Auranofin.

2. The method of claim 1, wherein the inhibitor of S-nitrosothiol breakdown is an inhibitor of gamma-glutamyltranspeptidase.

3. The method of claim 2, wherein the inhibitor of gamma-glutamyltranspeptidase is selected from the group consisting of L-gamma-glutamyl-(o-carboxy) phenylhydrazide, D-gamma-glutamyl-(o-carboxy) phenylhydrazide, acivicin and the combination of L-serine and borate.

4. The method of claim 1, wherein the inhibitor of S-nitrosothiol breakdown is an inhibitor of xanthine oxidase.

5. The method of claim 1, wherein the inhibitor of S-nitrosothiol breakdown is a chelator of copper and/or heme or non-heme iron.

6. The method of claim 1, wherein the inhibitor of S-nitrosothiol breakdown is an inhibitor of an enzyme or a non-enzymatic protein containing a thiol group and/or selenothiol group, which inhibitor is not a gold-containing compound.

7. A method for treating patients with mild or moderate asthma to inhibit progression to more severe asthma comprising administering to said patient a therapeutically effective amount of an inhibitor of S-nitrosothiol breakdown except for aurothioglucose, gold sodium thiomalate and Auranofin.

8. The method of claim 7, wherein the inhibitor of S-nitrosothiol breakdown is an inhibitor of gamma-glutamyltranspeptidase.

9. The method of claim 8, wherein the inhibitor of gamma-glutamyltranspeptidase is selected from the group consisting of L-gamma-glutamyl-(o-carboxy) phenylhydrazide, D-gamma-glutamyl-(o-carboxy) phenylhydrazide, acivicin, and the combination of L-serine and borate.

10. The method of claim 7, wherein the inhibitor of S-nitrosothiol breakdown is an inhibitor of xanthine oxidase.

11. The method of claim 7, wherein the inhibitor of S-nitrosothiol breakdown is a chelator of copper and/or heme or non-heme iron.

12. The method of claim 7, wherein the inhibitor of S-nitrosothiol breakdown is an inhibitor of an enzyme or a non-enzymatic protein containing a thiol group or a selenothiol group, which inhibitor is not a gold containing compound.

13. A method for treating a patient with asthma to ameliorate symptoms thereof comprising administering to said patient therapeutically effective amounts of NO donor and of an inhibitor of S-nitrosothiol breakdown.

14. The method of claim 13, wherein the NO donor is an S-nitrosothiol which is subject to breakdown by catalysts which cause S-nitrosothiol breakdown in asthma.

15. The method of claim 14, wherein the S-nitrosothiol has a molecular weight less than 150.

16. The method of claim 13, wherein the inhibitor of S-nitrosothiol breakdown is selected from the group consisting of inhibitors of gamma-glutamyl transpeptidase, inhibitors of xanthine oxidase, chelators of copper and/or heme iron, and inhibitors of enzymes and non-enzymatic proteins containing thiol groups and/or selenothiol groups.

17. A method for treating a patient with asthma to ameliorate symptoms thereof comprising administering to said patient a therapeutically effective amount of NO donor which is itself an S-nitrosothiol or which generates an S-nitrosothiol in vivo, which is resistant to breakdown by catalysts which cause S-nitrosothiol breakdown, with the proviso that the NO donor is not S-nitroso-N-acetylpenicillamine.

18. A method for treating patients with mild or moderate asthma to inhibit progression to more severe asthma comprising administering to said patient therapeutically effective amounts of an NO donor and of inhibitor of S-nitrosothiol breakdown.

19. The method of claim 18, wherein the NO donor is an S-nitrosothiol which is subject to breakdown by catalysts which cause S-nitrosothiol breakdown in asthma.

20. The method of claim 19, wherein the inhibitor of S-nitrosothiol breakdown is selected from the group consisting of inhibitors of gamma-glutamyl transpeptidase, inhibitors of xanthine oxidase, chelators of copper and/or heme iron, and inhibitors of enzymes and non-enzymatic proteins containing thiol groups and/or selenothiol groups.

21. A method for treating patients with mild or moderate asthma to inhibit progression to more severe asthma comprising administering to said patient a therapeutically effective amount of an NO donor which is itself an S-nitrosothiol or which generates an S-nitrosothiol in vivo, which is resistant to breakdown by catalysts which cause S-nitrosothiol breakdown, with the proviso that the NO donor is not S-nitroso-N-acetylpenicillamine.

* * * * *

UNITED STATES PATENT AND TRADEMARK OFFICE
CERTIFICATE OF CORRECTION

PATENT NO.   : 6,617,355 B1                                                      Page 1 of 1
DATED        : September 9, 2003
INVENTOR(S)  : Benjamin Gaston et al.

It is certified that error appears in the above-identified patent and that said Letters Patent is hereby corrected as shown below:

Column 1,
Line 11, after "HL52529" insert -- and 1R01HL059337 --

Signed and Sealed this

Sixteenth Day of December, 2003

JAMES E. ROGAN
*Director of the United States Patent and Trademark Office*